United States Patent
Pedersen

(10) Patent No.: US 6,811,479 B1
(45) Date of Patent: Nov. 2, 2004

(54) APPARATUS FOR THE CUTTING UP OF FISH, FILLETS OF FISH AND THE LIKE AND METHOD OF CUTTING UP OF FISH/FILLETS AND USE OF THE METHOD AND THE APPARATUS

(75) Inventor: Claus Mohr Pedersen, Hjorring (DK)

(73) Assignee: CP Food Machinery A/S, Hjorring (DK)

( * ) Notice: Subject to any disclaimer, the term of this patent is extended or adjusted under 35 U.S.C. 154(b) by 0 days.

(21) Appl. No.: 09/744,042

(22) PCT Filed: Jul. 19, 1999

(86) PCT No.: PCT/DK99/00413

§ 371 (c)(1),
(2), (4) Date: Mar. 15, 2001

(87) PCT Pub. No.: WO00/05968

PCT Pub. Date: Feb. 10, 2000

(30) Foreign Application Priority Data

Jul. 30, 1998 (DK) .......................................... 1998 00991

(51) Int. Cl.⁷ ............................................... A22C 25/16
(52) U.S. Cl. ..................................................... 452/161
(58) Field of Search .............................. 452/150, 161, 452/156, 157, 170, 177–184, 155

(56) References Cited

U.S. PATENT DOCUMENTS

| | | | | |
|---|---|---|---|---|
| 1,525,699 A | * | 2/1925 | Sullivan | 452/156 |
| 3,364,514 A | * | 1/1968 | Hartl et al. | 452/157 |
| 4,250,594 A | * | 2/1981 | Mitchell | 452/127 |
| 4,557,019 A | * | 12/1985 | Van Devanter et al. | 452/157 |
| 4,718,146 A | * | 1/1988 | Adkison | 452/152 |
| 5,094,650 A | * | 3/1992 | Schmidt | 452/161 |
| RE33,904 E | * | 4/1992 | Rudy et al. | 452/150 |
| 5,354,232 A | * | 10/1994 | Pontow | 452/182 |
| 5,395,282 A | * | 3/1995 | Harris et al. | 452/170 |
| 5,458,535 A | * | 10/1995 | Bullock et al. | 452/64 |
| 5,492,502 A | * | 2/1996 | Hjorth | 452/149 |
| 5,591,076 A | * | 1/1997 | Evers et al. | 452/157 |
| 5,871,395 A | * | 2/1999 | Grabau et al. | 452/161 |

FOREIGN PATENT DOCUMENTS

| | | | |
|---|---|---|---|
| DE | 2709152 B1 | * | 3/1978 |
| DE | 135798 | * | 4/1978 |
| GB | 1073779 | * | 6/1967 |
| SU | 1001-909 A | * | 3/1983 |

* cited by examiner

Primary Examiner—Peter M. Poon
Assistant Examiner—David Parsley
(74) Attorney, Agent, or Firm—William J. Sapone; Coleman Sudol Sapone, P.C.

(57) ABSTRACT

An apparatus for the cutting-up of fish, fish fillets and the like in slices etc., comprising a feeding unit which comprises a device for the feeding of fish/fillets, the feeding unit conveying the fish/fillets to a cutting unit which cuts the fish/fillets in slices, and a unit which comprises a device for the collection and processing of data, the collection and processing device comprises a device for the registration of the length of the fish/fillet in the feeding direction and/or the weight of the fish/fillet, and in that the feeding unit comprises a plane on which the fish/fillet is placed and fed forward, the plane forming a settable and adjustable angle to the horizontal plan, a device for the automatic adjustment and setting of the angle as a function of the length and/or the weight of the fish/fillet, and also a gripping device which comprises a device for the handling of the slices from the area in which the cutting takes place.

13 Claims, 3 Drawing Sheets

APPARATUS FOR THE CUTTING UP OF FISH, FILLETS OF FISH AND THE LIKE AND METHOD OF CUTTING UP OF FISH/FILLETS AND USE OF THE METHOD AND THE APPARATUS

BACKGROUND OF THE INVENTION

The invention concerns an apparatus for the cutting up of fish, fish fillets and the like in slices etc., comprising a feeding unit which comprises means for the feeding of the fish/fillets, said feeding unit conveying the fish/fillets to a cutting unit which cuts the fish/fillets in slices, and a unit which comprises means for the collection and processing of data. The invention also concerns a method of cutting up of fish/fillets and use of the method and the apparatus.

Different types of apparatus are known for the cutting of fish and fillets into slices. For example, there is known a German machine where the feeding of the fish/fillets takes place on a table which is moved in a rolling, upwards movement forwards to a cutting unit, and where the setting of the manner in which the cutting unit is to be activated is effected manually, in that the angle of the table and how the cutting unit is activated is controlled manually. This will give rise to a relatively great waste of fish and, moreover, it is not possible to achieve slices of uniform thickness and length, in that a given setting will result in the cutting unit being activated in a predetermined manner regardless of the dimensions of the fish/fillets, i.e. thickness and length.

From French patent application no. FR 2,627,423 and American patent publication no. U.S. Pat. No. 4,557,019, apparatus is known for the cutting up of e.g. fish in slices, and where each of which, comprises a measuring system for the measurement of uniform slices. However, these systems are relatively complicated, in that they comprise three-dimensional measuring units.

Moreover, the physical setting for achieving slices of a desired size is effected by regulating the angle of the knife in relation to the fish/fillet. This makes a subsequent automatic handling of the cut slices difficult, in that a gripping unit must be operated in relation to the position of the knife. A knife which thus changes position will make the subsequent handling difficult In this connection it should be noted that the publications thus do not deal with the whole of the problem concerning how the slices after being cut can and should be handled afterwards. Thus the systems do not invite a fully-automatic cutting up of the fish whereby uniform slices are achieved, and where these slices can subsequently be handled and packed following a previous programme.

BRIEF SUMMARY OF THE INVENTION

It is the object of the present invention to provide an apparatus which is not encumbered with the disadvantages of the known apparatus, and which can operate in a fully-automatic manner from the moment that fish/fillets are placed on the conveyor and until the packed slices are transported away, and where there is achieved an automatic regulation of the angle of the table on which the fish/fillets are placed, so that the cut slices are uniform, and whereby a minimum of wastage occurs by means of a simple and uncomplicated measurement, and where the subsequent handling of the cut slices is effected automatically.

This object is achieved with the apparatus disclosed in claim 1, where the apparatus comprises means for the collection and processing of data, said means comprising means for the registration of the length of the fish/fillet in the feeding direction and/or of the weight of the fish/fillet, and in that the feeding unit comprises a plane on which the fish/fillet is placed and fed forward, said plane forming a settable and adjustable angle to the horizontal plane, means for the automatic adjustment and setting of the angle as a function of the length and/or the weight of the fish/fillet, and also a gripping device which comprises means for the handling of the slices from the area in which the cutting takes place.

The setting is thus effected continuously by a form of iterative process during the transport of the fish/fillets. In that the fish/fillets have an approximately uniform appearance and cross-section regardless of the length and weight, it is possible by simple registrations, such as registration of the length and/or weight of the fish, to ensure that the size of the slice remains the same by effecting an adjustment of the angle of the feeding table in relation to the actual cutting arrangement, and where the knife of the cutting arrangement forms an inclined angle with the fish/fillet itself during the actual cutting process and with the horizontal plane. The slice size is to be understood as the thickness measurement and the length measurement in the feeding direction. It will thus be the case that all other things being equal, the more plane the table is to the horizontal the longer the slice achieved.

The fish/fillets are thus placed on the conveyor where the length and/or weight of each fish/fillet is determined, in that it is assumed beforehand that in longitudinal cross-section the same species of fish/fillets have the same uniform shape. When a given size is desired, it is possible regardless of the length to effect a continuous adjustment of the angle of the conveyor during the cutting process, so that the length of the slice remains the same for a given thickness, i.e. the more inclined the setting of the conveyor in relation to the cutting knife, the longer will be the slice cut longitudinally to the fish/fillet. Consequently, during the cutting of a fish/fillet, it is possible to continuously adjust the slope of the fish/fillet in relation to the knife, said knife being placed stationary in the cutting direction in relation to the horizontal plane and preferably placed at an angle of 10–20° in relation to this level. The slices are subsequently removed from the cutting area by means of a gripping arrangement, and are placed on a second conveyor with packaging.

By providing an apparatus according to the invention as disclosed in claim 2, the following is achieved. In that the length and/or weight of the fish/fillet is registered before activation of the cutting arrangement, the control unit is thus programmed with length and/or weight data which, together with data which arises via the means disclosed in claim 2, makes it possible to calculate when the cutting of the fish/fillet is finished. This results in the next fish unit being fed forward to the cutting arrangement, after which this fish unit is fed forward at that distance for which the machine has been set, and at that angle to which the plane is now regulated as a function of the dimensions and/or weight of the fish.

By providing an apparatus according to the invention as disclosed in claim 3 and 4, it is achieved that a slice which has been cut is removed quickly and effectively, unlike the known types of apparatus where the movement is exclusively linear. With the present invention, the movement consists of a combination movement where the movement pattern is partly linear and partly a turning movement whereby, all other things being equal, the interval of time necessary for the removal of a slice is considerably shorter.

By providing an apparatus according to the invention as disclosed in claim 5, it is achieved not only that the fish/fillet is secured in its position during the cutting, but also that the feeding takes place so that the fish/fillet is secured in its relative position on the conveyor.

The invention also concerns a method as disclosed in claim 8.

By using a method as disclosed, it is achieved that the fish/fillets are fed continuously to the cutting area where an automatic cutting of the fish/fillets is effected automatically. When the cutting has taken place, the slice is subsequently removed while at the same time the whole conveyor ensures that the fish/fillet which is being cut is moved the correct distance and at the right angle, so that with regard to thickness and length in the feeding direction, the next slice is of the same size as that slice which has just been cut.

At the moment that the cutting of the fish/fillet is finished, the conveyor describes a greater movement so that a new fish/fillet reaches forward to the cutting unit, in that the apparatus is arranged with a microprocessor which makes it possible to calculate, on the basis of the input it receives from various sensors and the data with which it is programmed, when the cutting of a fish/fillet is finished. Similarly, it can be calculated how long this new fish unit must be moved forward in steps and at which angle in order for the slices to be given the desired thickness and length.

In that a fish fillet does not have the same cross-sectional breadth area along the whole of its length, the angle for the same fish unit will typically be adjusted during the cutting, hereby ensuring the formation of the uniform slices.

There is hereby achieved a very continuous, automated process, where the dimension of the slices can be continuously regulated and with a minimum waste of fish/fillets, while at the same time a very high production speed is achieved, in that the cut pieces are immediately removed from the cutting area at the same time that the next piece is fed forward. Consequently, a minimum amount of time is wasted in connection with the process itself.

BRIEF DESCRIPTION OF THE DRAWINGS

The invention will now be explained in more detail with reference to the drawing, where.

DETAILED DESCRIPTION OF THE INVENTION

Figure 1:
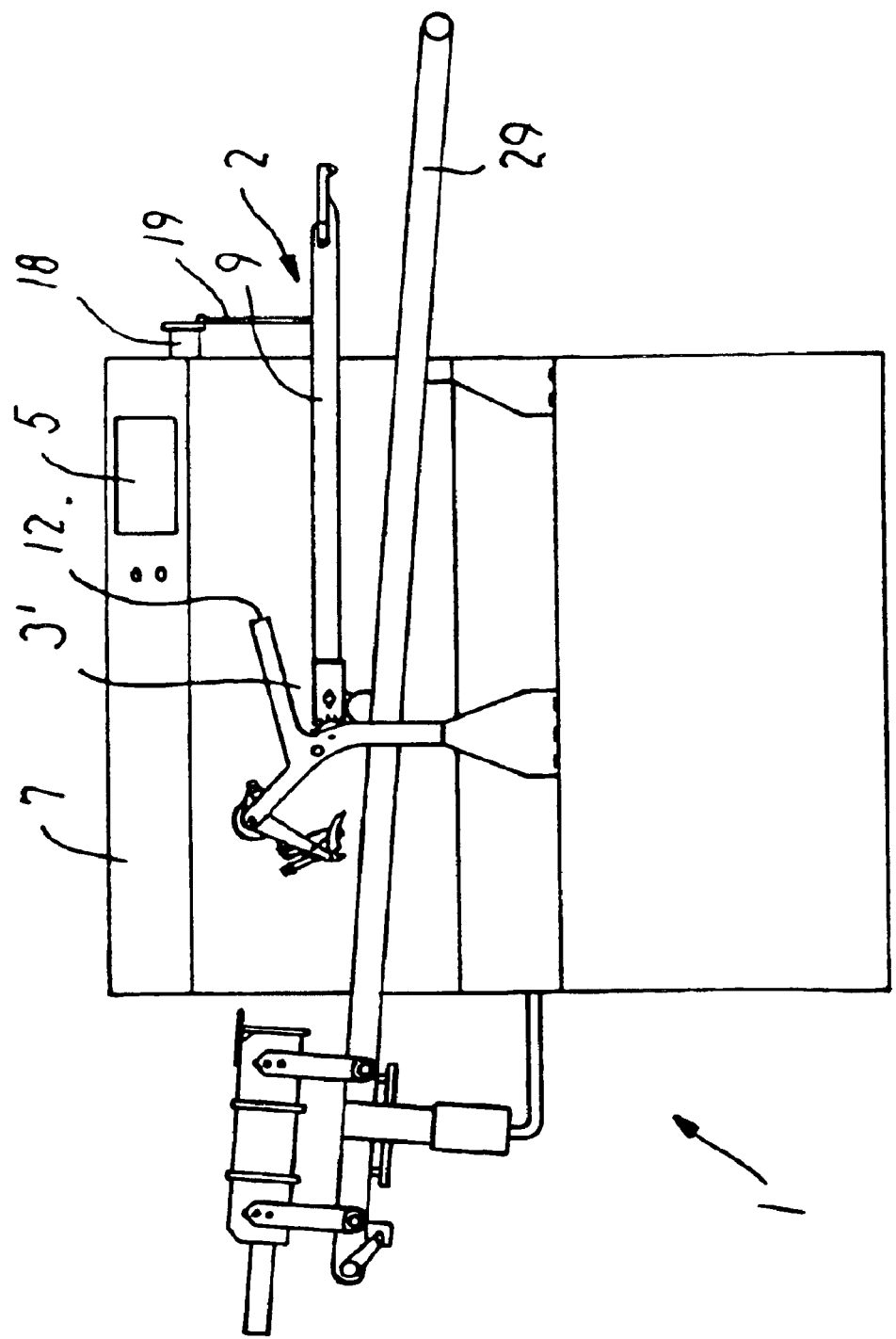
FIG. 1 shows the whole of the apparatus seen from the side.

FIG. 1 shows the whole of the apparatus 1 seen from the side, and thus comprising a feeding unit 2 which consists of a roller conveyor 9 on the surface of which the fish/fillets are placed. The angle of the roller conveyor 9 in relation to the horizontal plane can be adjusted by means of a spindle 19 which is driven by a motor 18, the setting of which in turn is controlled by a microprocessor 5 which constitutes an integrated part of a control unit 7. In the feeding direction the conveyor 9 terminates in a cutting area 3' which, with reference also to FIG. 2, comprises a cutting unit 3 which consists of a knife blade 30 with an edge 31 which faces in the same direction as the feeding direction and which is secured firmly between jaws 41,42. The cutter is preferably two rectangular pieces of metal with very sharp edges 31 which rub against each other, and the plane surface of the knife blade 30 forms an angle of 9–14° to the horizontal plane.

Figures 4A, 4B:
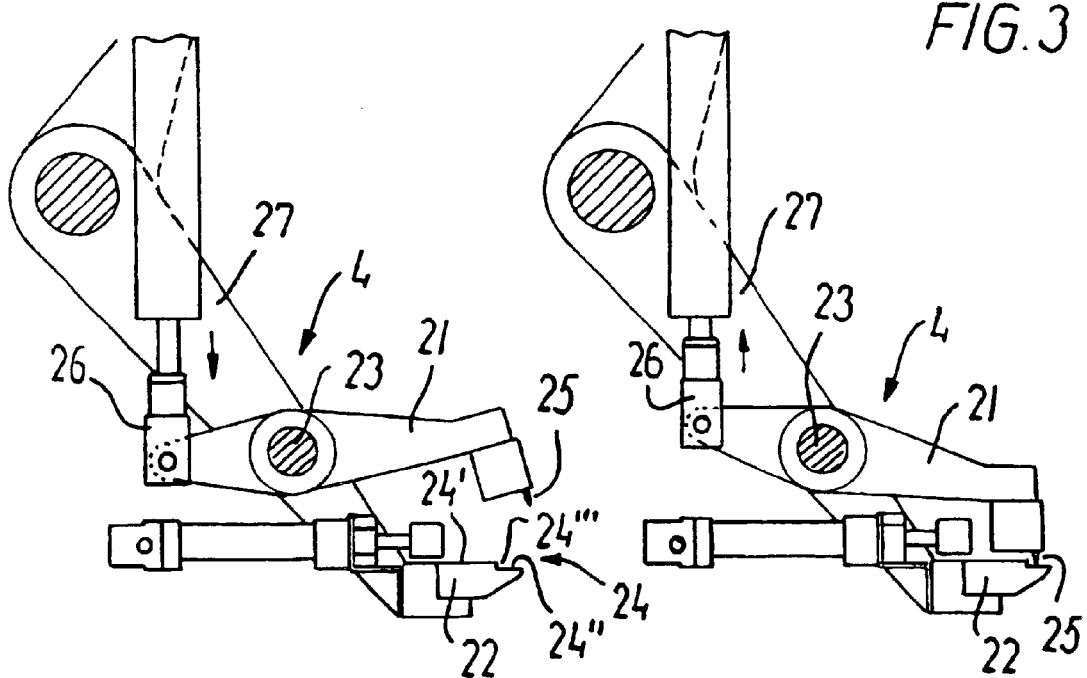

Guided in guide rails 20, the cutting unit 3 carries out its cutting function by a sliding and rapid movement down to where the fish lies to be cut, and where it is arranged to stop its movement when it reaches bottom, which corresponds to a form of edge 24''' provided in the cutting area, which will appear from FIGS. 4a and b. Hereafter, the knife 30 returns to its start position. The cutting area 3' also comprises a gripping device 4.

The construction of this gripping device will be explained with reference to FIGS. 4a and b. The gripping device 4 comprises a first jaw part 21 and a second jaw part 22, where the second jaw part 22 describes a linear and a rotating movement, while the first jaw part 21 describes rotating movement around an axis 23. The second jaw part 22 comprises a shelf area 24 in which the fish/fillet lies, and where the knife, when this reaches its end position during the cutting, has its edge up against the inner edge 24''', and the fish lies on both the upper 24' as well as the lower 24'' shelf which forms the edge 24'''. The more the fish lies on the upper shelf 24', the thicker will be the slice cut by the knife. The jaw part 21 comprises a kind of spikes 25 which secure the cut-off slice when this is removed from the cutting area 3' to the conveyor unit which carries away the cut-off slices.

As mentioned, the first jaw part 21 is pivotally connected via an axis 23 to a second arm 26 which, via a pneumatic system, is displaceable in a linear manner. In that the jaw part 21 is also pivotally connected at an angle to a third arm 27, a displacement of the second arm 26 via its pneumatic system will, when this arm is shortened, cause the first jaw part with its securing part 25 to bore down into the fish part which lies in the shelf area 24. Since the third arm 27 is fastened in its end position to the second jaw part 22, the upwards and rearwards movement of the third arm will cause the jaws 21,22, with the slice between them, to move away from the cutting area and over towards the packaging in which the slice is to be packed. When the arm 26 is extended by its pneumatic system, an opening will occur, and the jaw will thus release the slice which is secured between the first jaw part 21 and the second jaw part 22.

When a slice has been cut off, the first jaw part 21 is activated so that the securing element 25 bores down into the slice. This is effected by a shortening of the second arm 26, whereby rotation occurs around the axis 23. The cut-off slice is laid down on a conveyor as is seen in FIG. 1, where said conveyor is shown with the reference number 29, and on which the packaging units are placed, e.g. in the form of pieces of cardboard on which the cut-off slices are laid and transported away.

When a slice has been cut, the fish is moved a first distance so that the edge of the fish ends against the plateau 24' of the second jaw part 22. Synchronously with this movement, the conveyor is moved a second distance so that the next slice lies displaced in relation to the slice placed first on the cardboard piece.

Before the fish are conveyed completely up to the cutting area 3', their weights or their lengths have been registered, and the data is sent for registration in the unit 7 which collects data. The data is processed in a microprocessor 5, whereby a calculation is made of which angle the feeding unit in the form of the conveyor 2 must have in order to achieve a given desired thickness of the fish pieces. In that the fish pieces have a uniform cross-section seen in longitudinal section, this is a factor which is coded into the control unit, and which applies for all fish within a certain kind. With this data registered for the individual fish fillet, the fish is now fed further until it reaches a photocell area 12 which registers that the edge of the fish starts here, and which also registers when the fish has been fed completely through the area. This information is important for the microprocessor for this to be able to carry out a calculation of when a given fish is finished being cut, in that the data for said given fish gives rise to a quite certain angling of the conveyor.

The angle of the conveyor, which is adjusted by means of the spindle 19, will/can continuously change during the cutting of a single fish fillet, in that as mentioned earlier a fish fillet does not have a uniform cross-section, but an area where it is thicker than the remaining part. For the fish to be cut with the same length, such a thickened area will bring about a change in the angle of the conveyor 9, typically from an angle of around 10° to an angle of 20° during the whole of the sequence. It is hereby ensured that the length is maintained regardless of the size of the fish, whereby the actual size of each individual slice will be unchanged. The machine can thus be set for the cutting of slices of one, two, three mm and so on.

Figure 2:
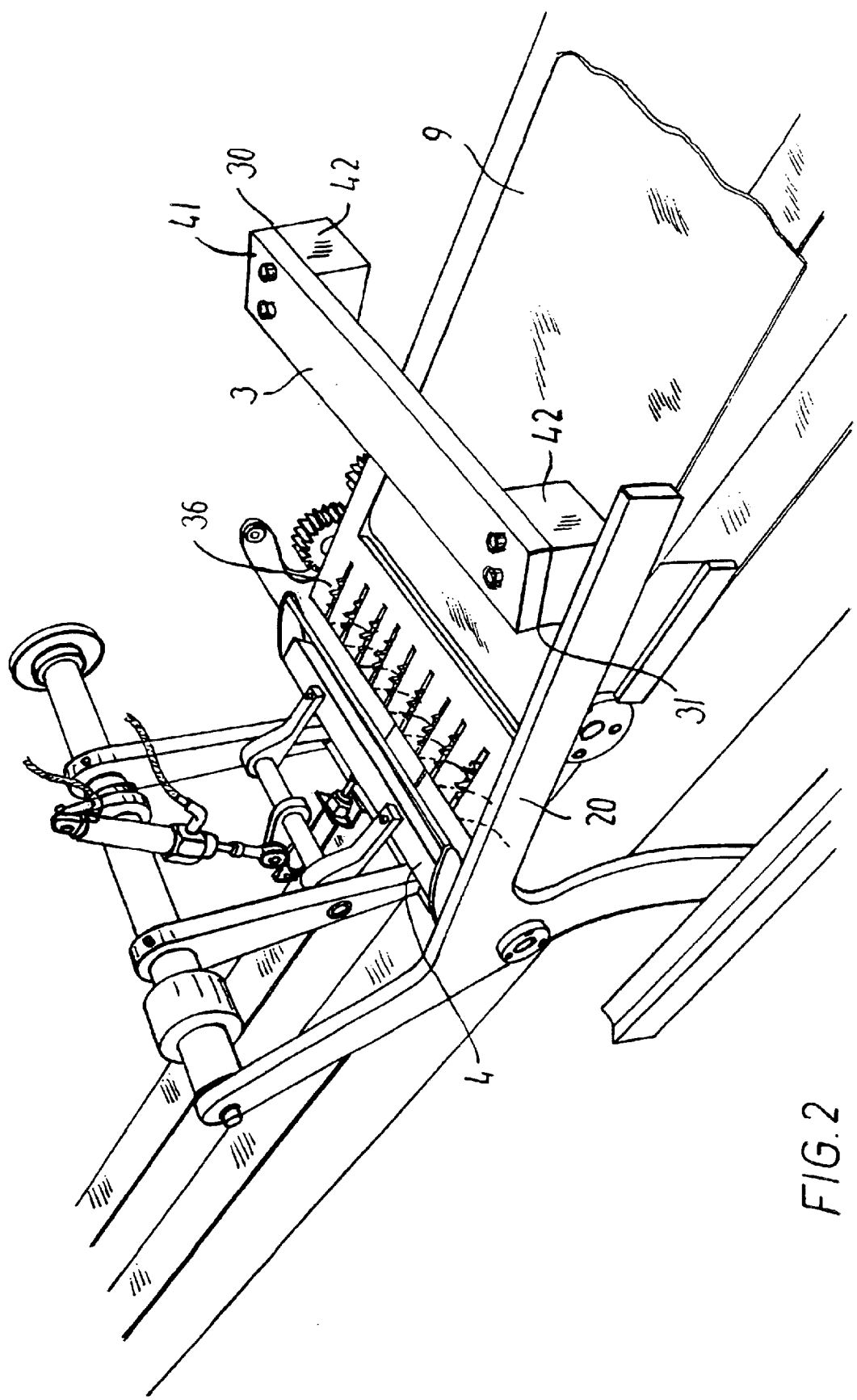
FIG. 2 shows details of the cutting area with cutting arrangement and gripping device seen obliquely from the side.

The cutting area 3' is shown in detail in FIG. 2, and comprises the knife itself 30 mounted in guide rails 20, and which reaches its end position in a rapid, snatching movement which corresponds to the edge 31 being in abutment with the edge 24''' in the second jaw part. The photocell 12, which registers the passage of the fish, is placed at a distance in front of the knife and in front of the gripping device.

Figure 3:
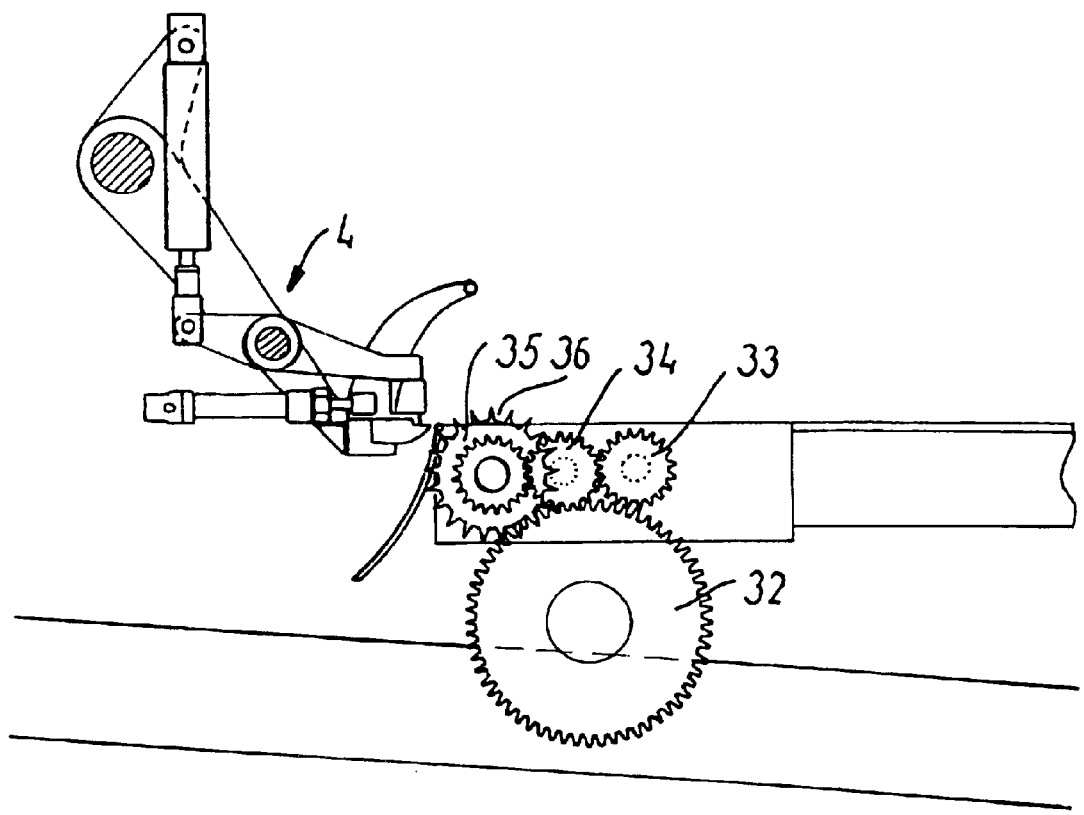
FIG. 3 shows a stylized view of the feeding arrangement and the gripping device, and FIGS. 4a and b show the gripping device in the open and the closed position respectively.

FIG. 3 shows in detail how the feeding takes place in relation to the gripping device 4. The feeding arrangement consists of a large gear wheel 32 which is driven by a motor. This gear wheel is in engagement with two further, smaller gear wheels, where the first smaller gear wheel 33 drives the actual conveyor and the second smaller gear wheel 34 drives a drum 35, the outer-periphery of which is provided with a number of barbs, said barbs 36 protruding up over the level of the conveyor in order to be able to bore up into that fish which is placed in the area before the cutting takes place. The object of this drum 35 mounted with barbs 36 is partly to secure the fish during the cutting and partly to assist with the further conveying forward of the fish piece.

It is envisaged that the system will be used primarily for the cutting up of fish, and here it is fresh and smoked fish which is contemplated (i.e. not frozen fish), and where the problem among other things is that the slices are relatively soft and difficult to handle, whereby it is difficult to have a system which secures the fish fillet in its position when the cutting takes place, and which at the same time ensures that the slices are cut without them becoming frayed and which are uniform in slice thickness and length.

The system overcomes these problems, while at the same time an automatic packing is effected, in that the gripping device takes care that the slices are laid down on the actual packing conveyor where preferably pieces of cardboard are moved past, and where an appropriate number of pieces are laid down, which can be pre-programmed in the microprocessor with the control unit.

It is envisaged that the system will be used for the cutting up of fresh/smoked salmon, where precisely the thickness and the length of the slices are of importance, partly to the producer and partly to the consumer.

What is claimed is:

1. An apparatus for cutting fish and fish fillets into slices comprising;
   a cutting unit for cutting the fish/fillets into slices made relative to a horizontal plane;
   a feeding unit having means for feeding the fish/fillets to the cutting unit, means for collecting and processing data on the fish/fillets having means for registering a length of the fish/fillet relative to a feeding direction and/or a weight of the fish/fillet, the feeding unit having an adjustable plane on which the fish/fillet is placed and fed forward, means for automatically adjusting and setting an angle of the plane, relative to the horizontal plane, responsive to the collecting and data processing means, continuously during cutting, the angle set as a function of the length and/or the weight of the fish/fillet for cutting the fish/fillet into a plurality of slices having an equal length for a given thickness, the apparatus having gripping means for removing each cut slice from the cutting area.

2. The apparatus according to claim 1, wherein a sensor unit is placed at a distance relative to the cutting unit and opposite to the feeding direction for registering a beginning and an end of each fish/fillet.

3. The apparatus of claim 2 wherein the sensor unit is a photocell.

4. The apparatus according to claim 1, wherein the gripping means comprise at least one jaw connected in a pivotal manner around an axis.

5. The apparatus according to claim 1, wherein the gripping means comprise at least one jaw part which is displaceable in a linear manner.

6. The apparatus according to claim 1, further comprising securing elements for securing the fish/fillet during cutting.

7. The apparatus according to claim 6, wherein the securing elements are wheels/drums having a periphery in which barbs are mounted which engage and secure the fish/fillet.

8. The apparatus according to claim 1, wherein the automatic angle adjustment means comprise a microprocessor.

9. The apparatus according to claim 1, wherein the means for setting the angle of the plane comprise a motor and a spindle to which the plane is mounted.

10. A method of cutting fish and fillets into slices made relative to a horizontal plane comprising;
    placing a fish/fillet on a feeding unit and conveying the fish/fillet to a cutting area;
    feeding the fish/fillet onto an angle adjustable conveyor in the cutting area;
    setting the angle adjustable conveyor at a given angle in relation to the horizontal plane, continuously adjusting the angle relative to each slice to provide each slice with a uniform length for a given thickness and continuously adjusting the angle during cutting of an individual slice;
    feeding the fish/fillet a given first distance until a sensor is activated;
    activating the cutting unit for horizontally cutting the slice;
    removing the slice from the cutting area, then, repeating the feeding, adjusting and cutting steps for each cut made thereafter to provide a plurality of slices of uniform length for a given thickness and continuously adjusting the angle during cutting of an individual slice;
    feeding the fish/fillet a given first distance until a sensor is activated;

activating the cutting unit for horizontally cutting the slice;

removing the slice from the cutting area, then, repeating the feeding, adjusting and cutting steps for each cut made thereafter to provide a plurality of slices of uniform length for a given thickness.

11. The method according to claim 10, further comprising using a gripping device to remove the slice from the cutting area, using a combined linear and rotating movement of the gripping device from a start position to an end position.

12. The method according to claim 11, further comprising, from the end position, returning the gripping device to the start position while moving the fish/fillet forward the given first distance.

13. The method according to claim 10, further comprising placing the plurality of slices into packaging, moving the packaging for a given second distance synchronously while moving the fish/fillet for the given first distance.

* * * * *